United States Patent [19]

Wan et al.

[11] Patent Number: 4,570,015

[45] Date of Patent: Feb. 11, 1986

[54] PREPARATION OF LARGE CRYSTALS OF N-BENZYLOXYCARBONYL-L-ASPARTIC ACID

[75] Inventors: K. Ming Wan, East Brunswick; Mary S. Chen; Clay T. Chen, both of Edison, all of N.J.

[73] Assignee: Hatco Chemical Corporation, Fords, N.J.

[21] Appl. No.: 526,580

[22] Filed: Aug. 26, 1983

[51] Int. Cl.$^4$ ............................................. C07C 125/06
[52] U.S. Cl. .................................................. 560/163
[58] Field of Search ......................................... 560/163

[56] References Cited

U.S. PATENT DOCUMENTS

| | | | |
|---|---|---|---|
| 3,808,190 | 4/1974 | Dahlmans | 560/163 |
| 4,293,706 | 10/1981 | Gorman | 560/163 |
| 4,345,091 | 8/1982 | Sugiyama | 560/163 |
| 4,450,284 | 5/1984 | Sathe | 560/163 |

OTHER PUBLICATIONS

Kirk–Othmer, "Encyclopedia of Chemical Technology," vol. 6, pp. 482–514 (1965).

*Primary Examiner*—Michael L. Shippen
*Attorney, Agent, or Firm*—Blum Kaplan Friedman Silberman & Beran

[57] ABSTRACT

N-Benzyloxycarbonyl-L-aspartic acid (Z-Asp) crystals several times larger than those obtained by conventional crystallization are prepared by acidifying an alkaline aqueous solution of a metal salt of Z-Asp at high temperatures of between about 20° to 45° C. The resulting large crystals contain less moisture and less impurities such as sodium chloride, dipeptide and benzyl alcohol, etc. than those crystals obtained at lower temperatures and they are easily processed for preparing aspartame.

14 Claims, No Drawings

PREPARATION OF LARGE CRYSTALS OF N-BENZYLOXYCARBONYL-L-ASPARTIC ACID

BACKGROUND OF THE INVENTION

This invention relates to the isolation of high quality N-benzyloxycarbonyl-L-aspartic acid (Z-Asp) which is suitable for use in the production of L-aspartyl-L-phenylalanine methyl ester(aspartame), an artificial sweetener. In particular this invention describes a method of preparing large crystals of relatively uniform size and high quality by acidifying an alkaline aqueous solution of the dialkali metal salt of Z-Asp at high temperatures.

Aspartame is known to be about 160 times sweeter than sucrose in aqueous solution. Thus, the use of aspartame as a low-calorie sweetener makes it a highly desirable end product. Aspartame is generally prepared from N-benzyloxycarbonyl-L-aspartic acid. In view of the end use of the aspartame in food products as a sugar substitute, the Z-Asp must be as pure as possible and substantially free of by-products. These impurities, such as the dipeptide, N-benzyloxycarbonyl aspartyl aspartic acid (Z-Asp-Asp), benzyl alcohol, benzyl cloride, benzaldehyde, dibenzyl carbonate and sodium chloride are generally formed during or prior to the formation of the Z-Asp.

The reaction of benzyl chloroformate (BCF) with L-aspartic acid (L-AA) to yield Z-Asp has been well known for a number of years. The chemical literature discloses that Z-Asp may be synthesized by the condensation of L-aspartic acid with benzyl chloroformate in an alkaline medium. Prior to 1981, the processes described in the literature did not mention the reaction conditions needed to produce Z-Asp with relatively small amounts of by-products.

U.S. Pat. No. 4,293,706 which issued on Oct. 6, 1981 to Gorman, et al. taught that Z-Asp can be prepared substantially free of Z-Asp-Asp by reacting benzyl chloroformate with the disodium salt of L-aspartic acid in an alkaline aqueous system within a specific pH range of between 10.75 and 11.75, and preferably 11.50 to 11.75 at 20°–25° C. After the reaction is completed, the reaction mixture is acidified with cooling. While maintaining the reaction mixture at 5°–10° C., concentrated acid is added until a pH of 1.5 to 2.5 is reached. This converts the Z-Asp dialkali metal salt to the free acid.

U.S. Pat. No. 4,345,091 issued on Aug. 17, 1982 to Sugiyama, et al. claims that high yields of Z-Asp can be prepared by allowing benzyl chloroformate to react with the sodium or potassium salt of L-aspartic acid and by carrying out the reaction with the pH maintained within the specific range of 12.0 to 13.5 throughout the reaction. Sugiyama, et al. teach maintaining the temperature of the reaction mixture at 10°–30° C. for 3 hours and they also suggest the use of organic solvents to remove any impurities in the system. After separating the organic layer from the reaction mixture, the aqueous layer is cooled and acidified with hydrochloric acid whereby Z-Asp is crystallized. In the sole working example the pH is adjusted to 1 with HCl, and the reaction mixture is allowed to stand overnight at 5° C.

Reaction conditions are very important in the production of a high purity Z-Asp in good yield. However, methods of separation and crystallization are equally important to obtain good products. When a Z-Asp aqueous reaction mixture is acidified with a mineral acid such as hydrochloric acid at low temperatures, the Z-Asp separates at about pH 3.5 as a thick heavy oil which becomes more viscous upon further acidification and it finally solidifies to a solid mass upon standing or upon agitation at the lower pH.

In a usual crystallization system which is initially homogenous, crystals are formed and separated directly from the solution and the impurities remain in the mother liquor. In the cases of patented Z-Asp processes the Z-Asp separates from the solution as an oily layer. According to the rule of thumb that like dissolves like, this oily layer carries with it most of the organic impurities present in the solution. In other words, impurities are dissolved and concentrated in the Z-Asp oily layer from which the Z-Asp crystallizes. The result is that simple crystallization cannot produce a high quality product directly from the reaction mixture. The quality of the product can be improved by extracting the reaction mixture with an organic solvent or by recrystallization of the crude product. These methods are time-consuming and cause significant loss in yield.

Both the Gorman, et al. and Sugiyama, et al. patentees provide suitable reaction conditions within narrow specific pH ranges for preparing a relatively pure Z-Asp with relatively small amounts of Z-Asp-Asp by-product. The patents do not discuss crystal size of the Z-Asp; nor do they suggest ways to improve yield, purity and product properties by increasing the size of the Z-Asp crystals or by any improvement in the manner of crystallization. Accordingly, it is desirable to provide a method for preparing Z-Asp crystals of increased crystal size and increased purity and high yield. The larger crystals are desirable because they are less dusty, they are more easily handled than smaller crystals, and they do not adsorb moisture as readily as small crystals on storage.

SUMMARY OF THE INVENTION

Generally speaking, in accordance with the invention, N-benzyloxycarbonyl-L-aspartic acid (Z-Asp) of larger crystal size and higher purity is obtained by acidifying an aqueous solution containing the dialkali metal salt of Z-Asp at relatively high temperatures. The aqueous solution is acidified with a mineral acid, such as hydrochloric or sulfuric, at elevated temperatures of between about 15° and 45° C. and to a pH below 2.5. Under these conditions Z-Asp forms a thin light oily liquid which is easily dispersed by agitation in the aqueous medium. The well-dispersed Z-Asp liquid droplets and the newly formed small Z-Asp crystals have comparatively large surface area, and thus increasing contact with the aqueous medium which continuously extracts the impurities from the Z-Asp droplets and the crystals. Under these circumstances, highly pure large crystals of Z-Asp are obtained after centrifugation and washing.

Alternatively, the small Z-Asp crystals obtained by acidification below 15° C. can be warmed with agitation to between about 15° C. and 45° C. to undergo the above mentioned solution-redeposition dynamic process and they are then cooled to 5°–10° C. These procedures lead to a product of higher quality with larger and relatively more uniform crystals after centrifuging and washing.

Large crystals of Z-Asp can also be obtained by feeding continuously and proportionally a Z-Asp reaction mixture and hydrochloric acid simultaneously to a pre-prepared Z-Asp crystalline slurry at a temperature of about 15°–45° C. and to a pH below about 2.5 with efficient agitation. The newly formed Z-Asp liquid crystallizes continuously and directly on the surface of existing crystals.

Large and high purity Z-Asp crystals can also be obtained by seeding. In this case the Z-Asp reaction mixture is kept at about 15°–45° C. and acidified to a pH below 2.5. Adding a small amount of Z-Asp crystals can accelerate the crystallization process and they also prevent the sudden solidification of the Z-Asp at lower temperatures.

The average crystal size obtained by any of the above methods is between 15 to 35 microns compared to 2 to 10 microns when acidification of the same reaction mixture is carried out at about 5°–10° C. Moreover, the products contain less moisture and less polar and nonpolar impurities, such as dipeptides, sodium chloride, benzyl alcohol, benzaldehyde and dibenzyl carbonate.

Accordingly, it is an object of the invention to provide an improved process for crystallizing Z-Asp from an aqueous medium of Z-Asp dialkali metal salt.

It is another object of the invention to provide a method for crystallizing Z-Asp from a reaction mixture by acidifying at relatively high temperatures.

It is a further object of the invention to provide an improved process for isolation of Z-Asp of increased crystal size.

Still another object of the invention is to provide an improved process for obtaining Z-Asp crystals containing reduced amounts of sodium chloride.

Still a further object of the invention is to provide a method for isolating Z-Asp crystals containing reduced amounts of Z-Asp-Asp.

Still another object of the invention is to provide a method for isolating Z-Asp crystals containing reduced amounts of benzylalcohol, benzaldehyde and dibenzyl carbonate.

It is another object of the invention to provide an improved process for isolating Z-Asp crystals containing reduced amount of water which facilitates drying.

It is a further object of the invention to provide an improved process for crystallizing Z-Asp from an aqueous mixture in increased yields.

Yet another object of the invention is to provide an improved process of crystallizing Z-Asp from a reaction mixture of benzyl chloroformate and a dialkali metal salt of L-aspartic acid.

Accordingly, it is an object of the invention to provide processes that improve the conditions of Z-Asp crystallization and which accelerate the displacement of impurities from Z-Asp crystals to the mother liquor so as to obtain high purity Z-Asp crystals.

It is another object of the invention to provide a simplified process for producing high purity Z-Asp without loss in yield.

It is a further object of the invention to provide an improved process for isolating large crystals of Z-Asp by warming to regrow small Z-Asp crystals previously obtained by acidification at low temperatures.

Still another object of the invention is to provide an improved process for isolating large crystals of Z-Asp continuously by feeding a Z-Asp reaction mixture to a pre-prepared Z-Asp crystalline slurry.

Still a further object of the invention is to provide an improved process for isolating large crystals of Z-Asp by adding Z-Asp seed crystals to a Z-Asp reaction mixture at about 15°–45° C. and at a pH below about 2.5.

Still other objects and advantages of the invention will in part be obvious and will in part be apparent from the specification.

The invention accordingly comprises the several steps and the relation of one or more of such steps with respect to each of the others, and the product possessing the features and properties which are exemplified in the following detailed disclosure, and the scope of the invention will be indicated in the claims.

DESCRIPTION OF THE PREFERRED EMBODIMENTS

N-Benzyloxycarbonyl-L-aspartic acid (Z-Asp) is the product of the condensation of benzyl chloroformate (BCF) and a dialkali metal salt of L-aspartic acid (L-AA) which is then acidified to convert the Z-Asp dialkali metal salt to the free acid. The condensation is in accordance with the following equation:

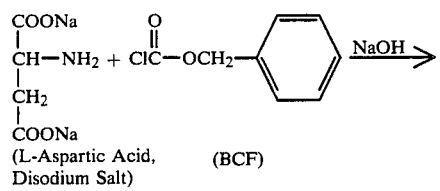

(L-Aspartic Acid, Disodium Salt)    (BCF)

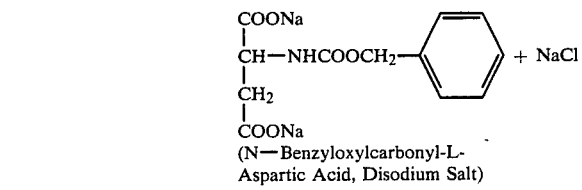

(N—Benzyloxylcarbonyl-L-Aspartic Acid, Disodium Salt)

The reaction may be carried out under a wide variety of appropriate reaction conditions. For example, the conditions taught in the Gorman, et al. or Sugiyama, et al. patents may be used which teach maintaining the pH of the reaction medium from 10.75 to 13.50 at temperatures varying from 0° to 40° C. Other reaction conditions are suitable which result in the Z-Asp dialkali metal salt in an alkaline aqueous reaction mixture. If an organic solvent is added to the reaction mixture, the aqueous phase containing the metal salt of the N-benzyloxycarbonyl-L-aspartic acid is separated from the organic solvent and it is then treated in accordance with the invention for the isolation of the Z-Asp crystals.

In accordance with the invention, the aqueous layer containing the Z-Asp dialkali metal salt is acidified with mineral acid at an elevated temperature at about 15°–45° C. The acid is hydrochloric or sulfuric. Preferrably, the acid utilized is hydrochloric and it is added to the reaction mixture which is maintained between about 25°–40° C. The acid is added until the pH fluctuation is stabilized, which is usually between about 0.5 to 2.5. Generally, acid is added until a pH between about 1.0 to 2.0 is reached.

After the addition of the acid, the temperature of the aqueous mixture is permitted to drop to room temperature over a period of several hours. The mixture is then cooled to between about 5° and 10° C. for several hours. The resulting Z-Asp crystals may be collected by centrifugation and then washed with ice water. The amount of ice water may vary, but it is generally between about ⅓ to 2.0 times the weight of the collected crystals. Preferably, the crystals are washed with an equal weight of ice water. The wet product generally contains between about 10–20% moisture which is removed in an oven at between 35° to 55° C.

Z-Asp crystals recovered in this manner generally have a much larger crystal size than if the crystals are recovered by the conventional techniques taught in the prior art. These prior art techniques provide for cooling the reaction mixtures to 5°–10° C. and maintaining this temperature during acidification. For example, Z-Asp crystals obtained in accordance with the invention generally are rhombic or rod shape having an average size of between about 15 to 35 microns. In contrast, conventional crystallization techniques provide amorphous material having an average particle size between about 2 to 10 microns.

As described above, the present invention includes at least four embodiments of crystallization processes which are exemplified in detail in the following examples. Each embodiment when used alone or in combination will improve the separation and the crystallization of Z-Asp directly from its acidified aqueous reaction mixture and provide an improved Z-Asp product. This product consists of well-formed larger and relatively more uniformly sized crystals of high quality with decreased amount of impurities. When this kind of Z-Asp product is used for aspartame synthesis, a better product is obtained in higher yield.

The newly developed process in accordance with the invention has the following advantages over conventional crystallization methods, such as those described in U.S. Pat. Nos. 4,293,706 and 4,345,091.

1. The high temperature process yields a well-formed large and relatively uniform crystalline Z-Asp which is less dusty, more stable, more easily dried and easier to handle.

2. The well-formed large and relatively uniform Z-Asp crystals are of high quality and desirable for aspartame synthesis. The crystals contain less impurities which are undesirable and detrimental in aspartame synthesis. These impurities are Z-Asp-Asp, benzyl alcohol, benzyl chloride, benzaldehyde, dibenzyl carbonate, sodium chloride and other known or unknown impurities detectable by HPLC, thin layer chromatography and wet analysis.

3. The alternative embodiments of the invention are simple and straight forward and offer a high quality Z-Asp product without resorting to conventional time-consuming, loss-causing and costly recrystallization and/or solvent extraction methods.

4. The alternative embodiments offer an improved Z-Asp product with a higher yield when compared with conventional crystallization methods.

5. The invention can also be applied successfully to the crystallization of low quality reaction products that contain extraordinary amounts of impurities, such as Z-Asp-Asp, benzyl alcohol, benzyl chloride and the like and/or reaction mixtures highly contaminated with organic solvents. For example, reaction mixtures containing up to 1.0 to 1.2% of Z-Asp-Asp can be converted to a product containing only about 0.2% of Z-Asp-Asp in accordance with the invention without resorting to recrystallization and/or solvent extraction.

6. The higher temperature facilitates the transfer of impurities from the oily liquid Z-Asp to the aqueous medium and makes the crystallization easier to initiate. For example, Z-Asp that has been crystallized from the aqueous reaction mixture at a temperature above 35° C. can be dried at about 35° C., while the Z-Asp produced by the conventional low temperature crystallization method will often melt upon drying above 35° C. These differences show that the products obtained in accordance with the invention are much purer and contain less impurities than the products which result from conventional low temperature crystallization. The products obtained from this invention dry more easily in a shorter period of time.

7. Small crystals obtained by low temperature crystallization below 15° C. may be heated with agitation in accordance with the invention to provide larger and more uniform crystals.

8. There is no strict limit on pH below 2.5. A pH approaching 2.5 can be used to slow the crystallization process for easier control.

9. The invention can be used successfully in a wide variety of situations, such as an automatically controlled continuous production line, and it provides an easily dried, high quality product of large crystals. Additionally, it offers the best choices to fit the most diversified needs in practical mass-production, e.g. from batch to continuous, from manual to semi-automatic to fully automatic, from high quality reaction mixtures to extraordinarily impure or contaminated reaction mixtures.

The following comparative examples illustrating the development and recovery of Z-Asp crystals from an aqueous medium in accordance with the invention are presented by way of illustration only, and are not intended in a limiting sense. The comparative starting materials are obtained in each instance from the same Z-Asp reaction mixture.

In most cases the Z-Asp dialkali metal salt was prepared in a 1 liter multi-necked flask equipped with a reflux condenser, two dropping funnels, a thermometer, a pH probe and a mechanical stirrer. L-Aspartic acid and water were charged into the flask and a 25% NaOH solution was added with stirring until the L-aspartic acid was fully dissolved. Benzyl chloroformate was added to the reaction mixture with sufficient sodium hydroxide solution to maintain the reaction mixture within the desired pH range. After the reaction was completed, each reaction mixture was separated into two equal portions and the Z-Asp was isolated under the conditions set forth in TABLE I. The temperatures of the crystallizations were controlled as shown in TABLE I. The product analyses are also set forth.

EXAMPLE 1

On a small scale, about 0.300 mole of Z-Asp disodium salt was prepared in accordance with the reaction conditions set forth in Gorman, et al. (U.S. Pat. No. 4,293,706). The temperature of the reaction mixture was maintained at 20° C. and the pH between 10.75 and 11.75. The resulting reaction mixture was separated into two equal parts of 170 ml. The assay determined by HPLC was 20% Z-Asp, 0.75% benzyl alcohol and 0.23% dipeptides.

Sample 1-A was placed in a multi-necked flask fitted with a thermometer, pH probe, additional funnel and mechanical stirrer and heated to 35° C., with stirring. Upon acidification to pH 2.5 with concentrated HCl, the temperature rose temporarily to 40° C. due to the heat of neutralization. After cooling to 37° C., the solution was seeded with about 50 mg of Z-Asp. Crystals appeared at 37°–38° C. and the temperature was raised to 42° C. during the crystallization process. The reaction mixture was gradually cooled to 7° C. with stirring while additional HCl was introduced gradually until pH 2.0 was reached. The reaction mixture was centrifuged at 2300 RPM until no water was collected. The weight of the centrifuge cake was 43 g and about 3 g was used for analysis. After washing the crude product with 46 ml of ice water, the crystals weighing about 40 g were dried overnight at 40° C. The dried product weighed 34 g, representing a yield of 91%.

Sample 1-B was treated as described in Gorman, et al's procedure. The temperature of crystallization was about 5°–10° C. The wet product was centrifuged at the same time and at the same speed as Sample 1-A to provide a direct comparison. The weight of the centrifuge cake was 47 g. About 3 g of the crude product was taken out for analysis and the rest was washed with 46 ml of ice water. The wet product was dried at 30° C. for 24 hours to remove part of the water and it was then dried overnight at 40° C. The dry product weighed 31 g representing a yield of 84%. All of the analytical results are summarized in Table 1.

Based on the results, the Z-Asp obtained by high temperature crystallization offers many advantages as compared to the products obtained by the conventional process. The crude product contains less moisture. It is easier to dry and does not require a stage dryer. The large crystals of dry product not only are several times larger, and henceforth less dusty and easier to handle; they also contain less impurities, such as dipeptide, benzyl alcohol and sodium chloride, and they are obtained in higher yields.

Of considerable significance are the final product analyses which show Sample 1-A crystal size of 25 to 35 microns with 0.06% dipeptides and 0.1% sodium chloride in comparison to the Sample 1-B crystal size of 2–4 microns with 0.08% dipeptides and 0.70% sodium chloride.

EXAMPLE 2

A stock solution of 51.22 Kg of an aqueous layer containing the disodium salt of Z-Asp was prepared from 5.00 Kg of L-aspartic acid. The reaction was run between 46°–48° C. at pH 10.50–10.75 using 1,1,1-trichloroethane as a solvent and $Na_2CO_3$ as a buffer. This solution was used for some of the subsequent examples.

An aliquot of 50.22 Kg of the above solution was divided into two equal parts designated Solution A and Solution B. Solution A was kept at 28° C. and pH 1.5 by the addition of concentrated HCl. When crystallization began, the slurry was warmed to about 35° C. for 2-3 hours with stirring. After cooling the reaction mixture to 5° C., the product was isolated by centrifugation and washed by spraying with 8 liters of 0.04% pre-cooled HCl solution. The average size of the resulting crystals was 25–30 microns. The dry product weighed 4.68 Kg, about 95% yield, and it contained less impurities than the product obtained from Solution B.

Solution B was crystallized at 5°–10° C. at pH 1.5. The size of the crystals was about 4–10 microns. The dry product weighed 4.50 Kg, about 92% yield and it contained relatively more impurities than the product obtained from Solution A. The results are summarized in Table 1.

EXAMPLE 3

From the stock solution in Example 2, 468 g was divided into two equal portions. Portion A was acidified to pH 1.1 rather rapidly with concentrated HCl and the temperature rose from 25° to 38° C., and about 30 mg of Z-Asp was added. The mixture was allowed to cool to 34° C. and crystals started to form. The slurry was allowed to warm to 36° C., then 38° C. and it was maintained at this temperature for 1.5 hours. The solution was permitted to cool and the crystallization was completed at 5°–7° C. between pH 1.1–1.4. The crude product was washed with 35 ml of ice water. The wet product required about 5 hours at 35°–40° C. in a vacuum desiccator to dry. The average crystal size of the final product was 25–35 microns.

Portion B was crystallized by adding HCl to the solution at 5°–7° C. between pH 1.1–1.4. The crude product separated as big lumps. It was suspended in 35 ml of ice-water and centrifuged under the identical conditions as Sample 3-A. The wet product required 8 hours to dry. The average particle size of the product was 4–6 microns and it contained more impurities than the crystals obtained from Portion A. The results are summarized in Table 1.

EXAMPLE 4

The same quantities of reactants and equipment were used as in Example 1, except that the reaction temperature during the preparation of Z-Asp was maintained between 30° and 35° C. with the pH at 10.5 to 11.5.

The reaction mixture was separated into two 170 ml samples and the crude Z-Asp was recovered by crystallization under the conditions set forth in Table 1. Both samples were centrifuged under the same conditions and then washed with 40 ml ice water. Previous attempts to dry Sample 4-B directly after centrifugation at 40° C. caused the product to fuse. Under these conditions the purity dropped to 97% from 99%. No such problems were encountered with the product of Sample 4-A which was dried at 40° C. The final properties of Z-Asp products are set forth in TABLE 1.

EXAMPLE 5

From 72.0 g (0.54 mole) of L-aspartic acid and a corresponding amount of BCF, an alkaline aqueous mixture of about 600 ml was prepared at 50°–55° C. between pH 9.0–10.0. After contaminating the reaction mixture deliberately with a small amount of benzyl alcohol and dipeptide as impurities, it was divided into two equal parts. A small portion of Part A was added to a beaker containing 100 ml of dilute HCl (about 1% by volume with $H_2O$) until the pH rose to above 1.0. It was warmed to 34° C., with stirring. Concentrated HCl and the rest of Part A were added simultaneously at 30°–38° C. between pH 1.30 to 1.40. After all the solution was added, it was maintained at 34° C. for 1.0 hour and it was gradually cooled to 10° C. at pH 1.20. The average crystal size of the dry product was 15 to 20 microns.

Part B was crystallized at 5°–7° C. between pH 0.70–1.20 by adding HCl to the solution. The crystal size of the product was 2 to 4 microns. The Part B product contained more impurities and it was obtained in lower yield than the product obtained from Part A. The results are summarized in Table 1.

TABLE 1

| Example | Crystallization Conditions Temp °C | pH | Crude Product Analysis Moisture+ % | Yield % | (g) | Crystal+++ Size μ | Purity+ % | Dipeptides++ % | BzOH++ % | NaCl+ % | Moisture+ % | Other++ Impurities % |
|---|---|---|---|---|---|---|---|---|---|---|---|---|
| 1-A | 34–40 | 1.35–2.00 | 17 | 91.0 | 34 | 25–35 | 99.85 | 0.06 | trace | 0.10 | 0.4 | 0.24 |
| 1-B | 5–10 | 1.60–2.10 | 25 | 84.0 | 31 | 2–4 | 99.40 | 0.08 | 0.09 | 0.70 | 0.4 | 0.32 |
| 2-A | 28–35 | 1.50–1.60 | 17 | 96.0 | 46800 | 25–30 | 99.52 | 0.11 | 0.05 | 0.02 | 0.4 | 0.09 |
| 2-B | 5–10 | 1.50–1.60 | 20 | 92.0 | 45000 | 4–10 | 98.47 | 0.15 | 0.41 | 1.20 | 0.4 | 0.16 |
| 3-A | 34–38 | 1.10–1.40 | 17 | 94.5 | 43.2 | 25–35 | 98.81 | 0.14 | 0.07 | 0.63 | 0.4 | 0.06 |
| 3-B | 5–7 | 1.10–1.40 | 25 | 89.9 | 41.1 | 4–6 | 99.15 | 0.17 | 0.35 | 1.26 | 0.4 | 0.10 |
| 4-A | 35–40 | 1.10–1.70 | 20 | 93.7 | 36.5 | 20–40 | 98.91 | 0.16 | 0.1 | 0.3 | 0.4 | 0.12 |
| 4-B | 10 | 1.10–1.70 | 22 | 89.5 | 34.8 | 4–7 | 99.01 | 0.28 | 0.8 | 0.8 | 0.4 | 0.17 |
| 5-A | 35–42 | 0.10–1.20 | 17 | 90.4 | 65.1 | 15–20 | 98.85 | 0.19 | 0.18 | 0.08 | 0.4 | 0.11 |
| 5-B | 5–7 | 0.70–1.20 | 25 | 88.6 | 63.8 | 2–4 | 98.00 | 0.24 | 2.30 | 0.77 | 0.4 | 0.18 |

+Analyzed by titration
++Analyzed by high pressure liquid chromatography, in area %
+++Measured by microscope Based on the comparative results, it can be seen that when Z-Asp is isolated from an alkaline aqueous reaction mixture substantially larger and purer crystals are obtained when the acidification is carried out at higher temperatures and an average crystal size on the order of 15 to 35 microns is obtained as compared to an average crystal size of up to about 2–10 microns when crystallization is carried out at conventional temperatures of about 5° C. to 10° C.

In sum, the larger size Z-Asp crystals obtained in accordance with the invention provide many advantages. These advantages are as follows:

1. Large crystals are less dusty and easier to handle;
2. Large crystals do not pick up moisture as readily as small crystals on storage;
3. Large crystals contain less sodium chloride;
4. Benzyl alcohol and other impurities are more easily washed from larger crystals;
5. Large crystals contain less dipeptide;
6. Drying time is shorter for larger crystals;
7. Stage drying is avoided because of lower moisture content of large crystals; and
8. Yield of Z-Asp is increased as less water is necessary to wash out impurities from large crystals.

It will thus be seen that the objects set forth above, among those made apparent from the preceding description, are efficiently attained and, since certain changes may be made in carrying out the above process and in the described product set forth without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

What is claimed is:

1. In a method of preparing large crystals of N-benzyloxycarbonyl-L-aspartic acid from an alkaline aqueous solution of a dialkali metal salt of N-benzyloxycarbonyl-L-aspartic acid by adding an acid to the aqueous solution, the improvement which comprises the step of carrying out the crystallization by elevating the temperature to about 25°–45° C. at a time the solution is acidified to a pH less than about 2.5, wherein the average particle size of the crystals obtained is larger than the crystals obtained when the alkaline aqueous solution of the dialkali metal salt is acidified at a temperature below about 25° C.

2. The method of claim 1, wherein the temperature is elevated to about 28°–42° C.

3. The method of claim 1, wherein the step of elevating the temperature to about 25°–45° C. is carried out by warming the aqueous solution prior to acidifying to lower the pH of the warm solution and maintaining the temperature of the alkaline aqueous solution at about 25°–45° C. when the pH is reduced to a pH of less than about 2.5.

4. The method of claim 1, wherein the step of elevating the temperature to about 25°–45° C. is carried out after adding the mineral acid to the aqueous solution at a temperature below about 15° C. to produce small crystals of N-benzyloxycarbonyl-L-aspartic acid and further including the steps of mixing the heated solution and cooling to below about 10° C. to form large crystals of N-benzyloxycarbonyl-L-aspartic acid.

5. The method of claim 1, wherein the steps of elevating the temperature of the alkaline aqueous solution to about 25°–45° C. and acidifying to a pH of less than about 2.5 is carried out by adding the alkaline aqueous solution and an acid simultaneously to a crystalline slurry of N-benzyloxycarbonyl-L-aspartic acid which is maintained at a temperature between about 25°–45° C.

6. The method of claim 1, wherein the temperature of the solution is maintained between about 25°–45° C. after acidification to a pH of below about 2.5 and adding to the solution seed crystals of N-benzyloxycarbonyl-L-aspartic acid.

7. The method of claim 1, wherein the dialkali metal salt is the disodium salt of N-benzyloxycarbonyl-L-aspartic acid.

8. The method of claim 1, wherein the acid is a mineral acid.

9. The method of claim 8, wherein the mineral acid is selected from the group consisting of hydrochloric acid and sulfuric acid.

10. The method of claim 8, wherein the mineral acid is HCl.

11. The method of claim 2, wherein the dialkali metal salt is the disodium salt of N-benzyloxycarbonyl-L-aspartic acid.

12. The method of claim 11, wherein the acid is a mineral acid.

13. The method of claim 12, wherein the mineral acid is selected from the group consisting of hydrochloric acid and sulfuric acid.

14. The method of claim 12, wherein the mineral acid is HCl.

* * * * *